US00PP25021P2

(12) United States Plant Patent
Dummen

(10) Patent No.: US PP25,021 P2
(45) Date of Patent: Oct. 28, 2014

(54) ***SANVITALIA* PLANT NAMED 'DUESANTOGO'**

(50) Latin Name: *Sanvitalia procumbens*
Varietal Denomination: Duesantogo

(71) Applicant: Tobias Dummen, Rheinberg (DE)

(72) Inventor: Tobias Dummen, Rheinberg (DE)

(73) Assignee: Dümmen Group B.V., DeLier (NL)

( * ) Notice: Subject to any disclaimer, the term of this patent is extended or adjusted under 35 U.S.C. 154(b) by 58 days.

(21) Appl. No.: 13/815,028

(22) Filed: Jan. 26, 2013

(51) Int. Cl.
*A01H 5/00* (2006.01)

(52) U.S. Cl.
USPC ..... Plt./476

(58) Field of Classification Search
CPC ..... A01H 1/00; A01H 3/00; A01H 4/00; A01H 5/00
USPC ..... Plt./476
See application file for complete search history.

*Primary Examiner* — Anne Grunberg
(74) *Attorney, Agent, or Firm* — C. A. Whealy

(57) ABSTRACT

A new and distinct cultivar of *Sanvitalia* plant named 'Duesantogo', characterized by its compact and mounding plant habit; vigorous growth habit; early and freely flowering habit; and large inflorescences with bright yellow-colored ray florets and yellow green-colored disc florets.

1 Drawing Sheet

Botanical designation: *Sanvitalia procumbens.*
Cultivar denomination: 'DUESANTOGO'.

BACKGROUND OF THE INVENTION

The present invention relates to a new and distinct cultivar of *Sanvitalia* plant, botanically known as *Sanvitalia procumbens*, and hereinafter referred to by the name 'Duesantogo'.

The new *Sanvitalia* plant is a product of a planned breeding program conducted by the Inventor in Rheinberg, Germany. The objective of the breeding program is to create new compact and mounding *Sanvitalia* plants with numerous inflorescences.

The new *Sanvitalia* plant originated from a cross-pollination conducted by the Inventor in Rheinberg, Germany in July, 2009 of a proprietary selection of *Sanvitalia procumbens* identified as code number L08-0603-002, not patented, as the female, or seed, parent with a proprietary selection of *Sanvitalia procumbens* identified as code number F-20-025, not patented, as the male, or pollen, parent. The new *Sanvitalia* plant was discovered and selected by the Inventor as a single flowering plant from within the progeny of the stated cross-pollination in a controlled greenhouse environment in Rheinberg, Germany in May, 2011.

Asexual reproduction of the new *Sanvitalia* plant by vegetative cuttings in a controlled environment in Rheinberg, Germany since July, 2011 has shown that the unique features of this new *Sanvitalia* plant are stable and reproduced true to type in successive generations.

SUMMARY OF THE INVENTION

Plants of the new *Sanvitalia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Duesantogo'.

These characteristics in combination distinguish 'Duesantogo' as a new and distinct *Sanvitalia* plant:

1. Compact and mounding plant habit.
2. Vigorous growth habit.
3. Early and freely flowering habit.
4. Large inflorescences with bright yellow-colored ray florets and yellow green-colored disc florets.

Plants of the new *Sanvitalia* differ primarily from plants of the female parent selection in plant habit as plants of the new *Sanvitalia* are more compact than plants of the female parent selection.

Plants of the new *Sanvitalia* differ primarily from plants of the male parent selection in inflorescence size as plants of the new *Sanvitalia* have larger inflorescences than plants of the male parent selection.

Plants of the new *Sanvitalia* can be compared to plants of *Sanvitalia procumbens* 'Cuzco Ideal', not patented. In side-by-side comparisons conducted in Rheinberg, Germany, plants of the new *Sanvitalia* differed from plants of 'Cuzco Ideal' in the following characteristics:

1. Plants of the new *Sanvitalia* were more compact than plants of 'Cuzco Ideal'.
2. Plants of the new *Sanvitalia* had shorter internodes than plants of 'Cuzco Ideal'.
3. Plants of the new *Sanvitalia* had larger leaves than plants of 'Cuzco Ideal'.
4. Inflorescences of plants of the new *Sanvitalia* had larger ray florets than inflorescences of plants of 'Cuzco Ideal'.

BRIEF DESCRIPTION OF THE PHOTOGRAPH

The accompanying photograph illustrates the overall appearance of the new *Sanvitalia* plant showing the colors as true as it is reasonably possible to obtain in colored reproductions of this type. Colors in the photograph may differ slightly from the color values cited in the detailed botanical description which accurately describe the colors of the new *Sanvitalia* plant.

The photograph comprises a side perspective view of a typical flowering plant of 'Duesantogo' grown in a container.

DETAILED BOTANICAL DESCRIPTION

The aforementioned photograph and following observations and measurements describe plants grown during the summer in 10.5-cm containers in a glass-covered greenhouse in Rheinberg, Germany under conditions and practices which approximate those generally used in commercial *Sanvitalia* production. During the production of the plants, day and night temperatures averaged 18° C. and light levels averaged 4,500 lux. Plants were pinched one time three weeks after planting and were 20 weeks old when the photograph and description were taken. In the following description, color references are made to The Royal Horticultural Society Colour Chart, 1995 Edition, except where general terms of ordinary dictionary significance are used.

Botanical classification: *Sanvitalia procumbens* 'Duesantogo'.

Parentage:

*Female parent*.—Proprietary selection of *Sanvitalia procumbens* identified as code number L08-0603-002, not patented.

*Male parent*.—Proprietary selection of *Sanvitalia procumbens* identified as code number F-20-25, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; color, close to 155B.

*Rooting habit*.—Freely branching; dense.

Plant description:

*Plant and growth habit*.—Compact, upright, outwardly spreading and mounding plant habit; vigorous growth habit.

*Branching habit*.—Freely branching habit with two lateral branches potentially forming at every node.

*Plant height*.—About 9 cm.

*Plant diameter or spread*.—About 22 cm.

*Lateral branches*.—Length: About 12 cm. Diameter: About 2 mm. Internode length: About 2 cm. Strength: Strong, flexible. Texture: Pubescent. Color: Close to 144A.

Foliage description:

*Arrangement*.—Opposite, simple.

*Length*.—About 2.2 cm.

*Width*.—About 1 cm.

*Shape*.—Lanceolate to elliptical.

*Apex*.—Acute.

*Base*.—Obtuse.

*Margin*.—Entire.

*Texture, upper surface*.—Pubescent.

*Texture, lower surface*.—Smooth, glabrous.

*Venation pattern*.—Pinnate.

*Color*.—Developing and fully expanded leaves, upper surface: Close to 141A; venation, close to 144C. Developing and fully expanded leaves, lower surface: Close to 139C; venation, close to 144C.

*Petioles*.—Length: About 2.2 mm. Diameter: About 2 mm. Texture, upper and lower surfaces: Smooth, glabrous. Color, upper surface: Close to 144C. Color, lower surface: Close to 144D.

Inflorescence description:

*Form and aspect*.—Single (daisy) inflorescence form with ray and disc florets developing acropetally on a pyramidal receptacle; inflorescences positioned above and beyond the foliar plane on strong peduncles; inflorescences face mostly upright to outwardly.

*Flowering habit*.—Freely flowering habit; about 35 to 40 inflorescences develop per plant.

*Fragrance*.—None detected.

*Natural flowering season*.—Plants flower continuously from April to October in Germany; early flowering habit, plants begin flowering about six weeks after planting.

*Inflorescence longevity*.—Inflorescences last about four days on the plant; inflorescences persistent.

*Inflorescence buds*.—Height: About 3 mm. Diameter: About 4 mm. Shape: Oblong. Color: Close to 144A.

*Inflorescence size*.—Diameter: About 1.6 cm. Depth (height): About 5 mm. Disc diameter: About 5 mm. Receptacle diameter: About 1 mm. Receptacle height: About 1 mm. Receptacle color: Close to 144B.

*Ray florets*.—Number of ray florets per inflorescence: About twelve arranged in a single whorl. Length: About 5.3 mm. Width: About 4.4 mm. Shape: Elliptical. Apex: Emarginate or obtuse. Base: Cordate, oblique. Margin: Entire. Texture, upper and lower surfaces: Smooth, glabrous; satiny. Color: When opening and fully opened, upper surface: Close to 9A; color does not fade with development. When opening and fully opened, lower surface: Close to 9B and 144B.

*Disc florets*.—Number of disc florets per inflorescence: About 50. Length: About 3 mm. Diameter: About 1 mm. Shape: Tubular, elongated; apex dentate. Texture: Smooth, glabrous. Color, immature: Close to 144A. Color, mature: Apex: Close to 9A. Mid-section and base: Close to 144A.

*Phyllaries*.—Quantity per inflorescence: About ten to twelve in a single whorl. Length: About 4 mm. Width: About 3 mm. Shape: Ensiform. Apex: Acute. Base: Acute. Margin: Entire. Texture, upper and lower surfaces: Smooth, glabrous. Color, upper and lower surfaces: Close to 144A.

*Peduncles*.—Length, terminal peduncle: About 3.7 cm. Length, fourth peduncle: About 2.4 cm. Diameter: About 1 mm. Strength: Strong; flexible. Texture: Smooth, glabrous. Color: Close to 144A.

*Reproductive organs*.—Androecium (present on disc florets only): Quantity per disc floret: Two. Filament length: About 0.5 mm. Filament color: Close to 144D. Anther shape: Oblong. Anther length: About 1 mm. Anther color: Close to 1A. Pollen amount: Scarce. Pollen color: Close to 2A. Gynoecium (present on ray and disc florets): Pistil length: About 2 mm. Style length: About 0.5 mm. Style color: Close to 1A. Stigma shape: Bi-parted. Stigma color: Close to 1A. Ovary color: Close to 144B.

*Seeds*.—Quantity per inflorescence: About 50. Length: About 1 mm. Diameter: About 1 mm. Color: Close to 200B.

Disease & pest resistance: Plants of the new *Sanvitalia* have not been shown to be resistant to pathogens and pests common to *Sanvitalia* plants.

Garden performance: Plants of the new *Clematis* have exhibited good tolerance to rain and wind and have been observed to tolerate temperatures from about 5° C. to about 40° C.

It is claimed:

1. A new and distinct *Sanvitalia* plant named 'Duesantogo' as illustrated and described.

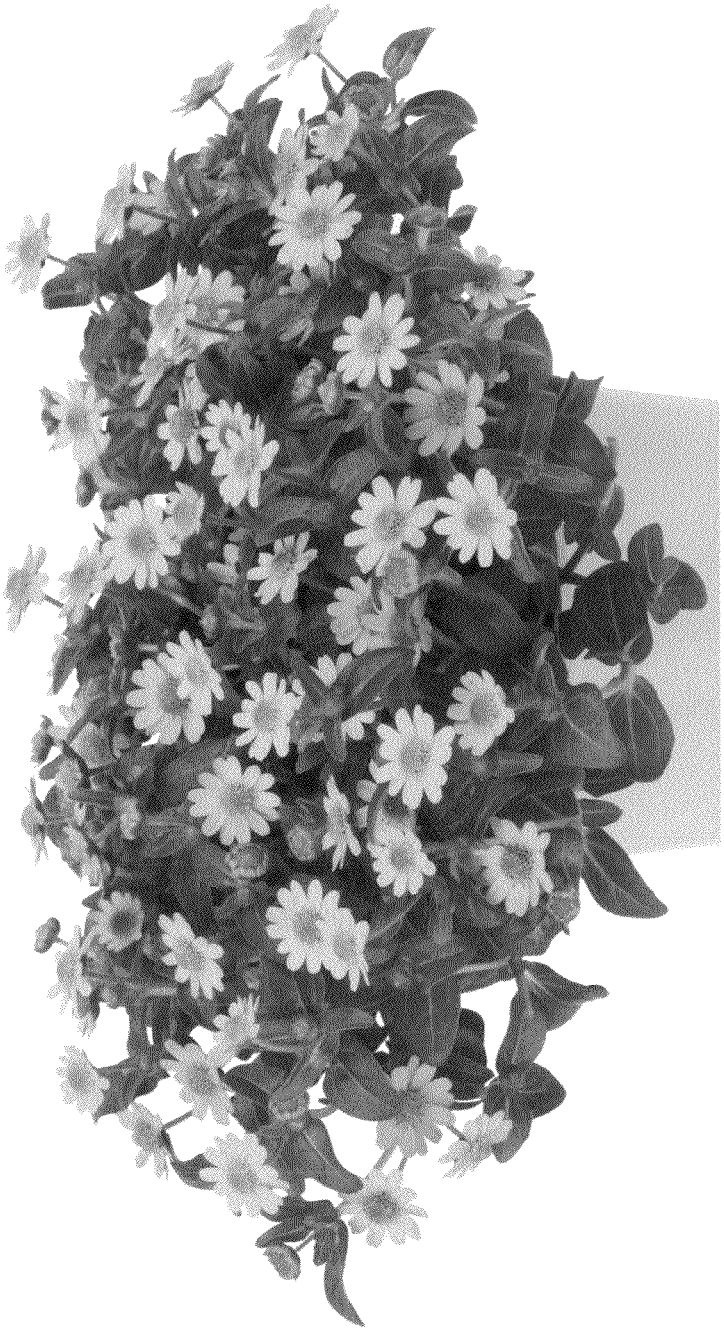

* * * * *